United States Patent [19]

Sturm

[11] Patent Number: 4,577,104

[45] Date of Patent: Mar. 18, 1986

[54] MEASURING THE PERCENTAGE OR FRACTIONAL MOISTURE CONTENT OF PAPER HAVING A VARIABLE INFRARED RADIATION SCATTERING CHARACTERISTIC AND CONTAINING A VARIABLE AMOUNT OF A BROADBAND INFRARED RADIATION ABSORBER

[75] Inventor: Steven P. Sturm, Columbus, Ohio

[73] Assignee: AccuRay Corporation, Columbus, Ohio

[21] Appl. No.: 572,361

[22] Filed: Jan. 20, 1984

[51] Int. Cl.$^4$ .............................................. G01J 1/00
[52] U.S. Cl. .................................... 250/339; 250/341
[58] Field of Search ................................ 250/339, 341

[56] References Cited

U.S. PATENT DOCUMENTS

| | | | |
|---|---|---|---|
| 3,405,268 | 10/1968 | Brunton | 250/341 |
| 3,551,678 | 12/1970 | Mitchell | 250/341 |
| 3,793,524 | 2/1974 | Howarth | 250/339 |
| 3,851,174 | 11/1974 | Dahlin | 250/339 |
| 4,052,615 | 10/1977 | Cho | 250/341 |
| 4,085,326 | 4/1978 | Williams | 250/339 |
| 4,097,743 | 6/1978 | Carlson | 250/339 |
| 4,171,918 | 10/1979 | Mactaggart | 250/339 |
| 4,300,049 | 11/1981 | Sturm | 250/339 |
| 4,306,151 | 12/1981 | Chase | 250/341 |
| 4,345,150 | 8/1982 | Yamura et al. | 250/339 |
| 4,363,968 | 12/1982 | McGowan et al. | 250/339 |

FOREIGN PATENT DOCUMENTS 2044443  3/1979  United Kingdom ................ 250/339

OTHER PUBLICATIONS

Brunton, D. C., "Measurement of Moisture in the Paper Industry," *Southern Pulp and Paper Manufacturer*, May 10, 1967, pp. 108, 109, 114, 116 and 117.

Primary Examiner—Alfred E. Smith
Assistant Examiner—Richard Hanig
Attorney, Agent, or Firm—C. Henry Peterson

[57] ABSTRACT

The moisture in paper is measured using a first set of infrared radiation wavelengths that have about the same absorption coefficients for the fiber constitutent of the paper but have substantially different absorption coefficients for the moisture contained in the paper, and a second set of infrared wavelengths that have about the same absorption coefficients for the moisture contained in the paper but have substantially different absorption coefficients for the fiber constituent, both sets of infrared radiation wavelengths being affected to about the same extent by a variable scattering characteristic of the fiber and are also affected to about the same extent by the variable amount of a broadband absorber such as carbon in the paper.

4 Claims, 2 Drawing Figures

MEASURING THE PERCENTAGE OR FRACTIONAL MOISTURE CONTENT OF PAPER HAVING A VARIABLE INFRARED RADIATION SCATTERING CHARACTERISTIC AND CONTAINING A VARIABLE AMOUNT OF A BROADBAND INFRARED RADIATION ABSORBER

TECHNICAL FIELD

This invention relates to an infrared radiation method and apparatus for measuring the moisture fraction or percent moisture contained in a traveling sheet of paper also containing a fiber constituent that may have a variable infrared radiation scattering characteristic and that may also include a variable amount of a broadband infrared radiation absorber such as carbon black.

More particularly the invention relates to a method and apparatus wherein two sets of infrared radiation wavelengths that are directed into the paper are affected to about the same extent by the variable scattering characteristic and are also affected to about the same extent by the variable amount of the broadband absorber. The wavelengths in the first set have about the same absorption coefficients for the fiber constituent, but have substantially different absorption coefficients for the moisture contained in the paper. The wavelengths in the second set have about the same absorption coefficients for the moisture contained in the paper but have substantially different absorption coefficients for the fiber constituent. Radiations, from the paper, having these wavelengths are detected and processed to produce a response that is indicative of the moisture fraction or percent moisture and is substantially independent of the variations in the scattering characteristic and in the amount of broadband absorber.

BACKGROUND ART

Methods and apparatus using two sets of infrared radiation wavelengths for measuring moisture fraction or percent moisture in paper are described in U.S. Pat. No. 3,405,268 Brunton. Where the paper contained heavy clay loadings, the method and apparatus was modified as described in an article by Brunton, D. C. entitled "Measurement of Moisture in the Paper Industry," *Southern Pulp and Paper Manufacturer*, May 10, 1967, pp. 108, 109, 114, 116 and 117.

The problem of measuring moisture in paper having variable scattering characteristics is specifically addressed in U.S. Pat. Nos. 3,793,524 Howarth, 3,851,175 Dahlin et al and 4,052,615 Cho. While the techniques disclosed in these patents reduce errors caused by variable scattering effects, they may enhance errors due to variable carbon black loading.

The problem of measuring moisture in paper having variable carbon black loading is specifically addressed in U.S. Pat. No. 4,306,151 Chase. While the techniques disclosed in this patent may reduce carbon loading errors, they may enhance errors due to variable scattering effects.

U.S. Pat. No. 4,085,326 Williams deals with the dual problem of a variable amount of carbon black and/or a variable amount of a scattering substance such as titanium dioxide in a plastic film whose thickness is measured by infrared reflection from the back side of the film. Such a reflection technique is not generally applicable to the measurement of paper moisture.

U.S. Pat. No. 3,551,678 Mitchell discloses a method and apparatus with a theoretical capability of dealing with either one or both of the problems of a variable scattering characteristic and a variable amount of carbon black in paper, so long as the amount of carbon black is not excessive. However, the difficulties of carrying out the invention in the manner disclosed, especially in the harsh industrial environments to which such instruments are subject, have in general prevented the theoretical advantages from being realized.

DISCLOSURE OF INVENTION

In accordance with this invention, there are provided methods and means adapted for measuring the moisture fraction or percent moisture contained in a traveling sheet of paper also containing a fiber constituent that may have a variable infrared radiation scattering characteristic and may include a variable amount of a broadband infrared radiation absorber, comprising method steps and elements of apparatus for directing into the paper two sets of infrared radiation wavelengths that are affected to about the same extent by the variable scattering characteristic and are also affected to about the same extent by the variable amount of the broadband absorber, the first set including wavelengths that have about the same absorption coefficients for the fiber constituent but have substantially different absorption coefficients for the moisture contained in the paper, the second set including wavelengths that have about the same absorption coefficients for the moisture contained in the paper but have substantially different absorption coefficients for the fiber constituent, detecting radiations from the paper, forming a function of the ratio of the transmittances of the detected radiations in the first set to produce a first response to the moisture contained in the paper, the first response including a first error function dependent on the scattering characteristic and broadband absorber content of the fiber constituent, forming a function of the ratio of the transmittances of the detected radiations in the second set to produce a second response to the fiber constituent, the second response including substantially the same first error function dependent on the scattering characteristic and broadband absorber content of the fiber constituent, the second response also including a second error function dependent on the amount of moisture contained in the paper, forming a function of the ratio of the first and second responses to produce a third response that is substantially independent of the first error function but is dependent on the second error function, and producing a fourth response which is a function of the third response, which is calibrated in accordance with the second error function, and which is indicative of the moisture fraction or percent moisture contained in the paper, substantially independent of the first and second error functions and substantially independent of variations of the scattering characteristic and variations in the amount of the broadband absorber.

BEST MODE FOR CARRYING OUT THE INVENTION

Figure 1:
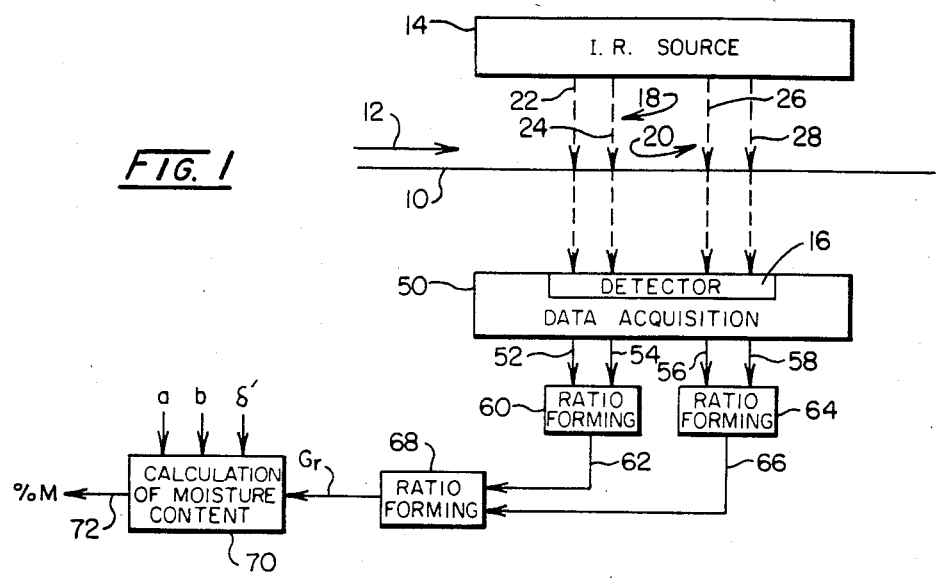
FIG. 1 is a schematic diagram illustrating a typical embodiment of the invention, combining both representations of typical structural elements and representations of typical information handling procedures.

Referring to FIG. 1, the numeral 10 indicates a traveling sheet of paper being produced continuously by a paper making machine. Typically the illustrated portion of the sheet 10 is moving in the direction of the arrow 12, from the calender stack (not shown) to the windup (not shown).

The moisture fraction or percent moisture contained in sheet 10 is measured by an infrared radiation gauging apparatus comprising a source means 14 and a detector means 16. The source means 14 directs into the paper sheet 10 two sets 18 and 20 of infrared radiation wavelengths.

Typically the first set 18 includes wavelengths 22 at about 1.83μ (1.83 microns) and wavelengths 24 at about 1.93μ. The second set 20 includes wavelengths 26 at about 1.89μ and wavelengths 28 at about 2.12μ. The total span of wavelengths is thus typically less than about 0.3μ. While the paper 10 may have a variable scattering characteristic for reasons set forth, for example, in U.S. Pat. Nos. 3,793,524, 3,851,175 and 4,052,615 supra, these wavelengths are affected to about the same extent by variations in the scattering characteristic, due to the nature and size of the scattering structures in the paper fiber. Similarly these wavelengths are affected to about the same extent by a variable amount of broadband absorber, typically carbon black, contained in the fiber.

Figure 2:
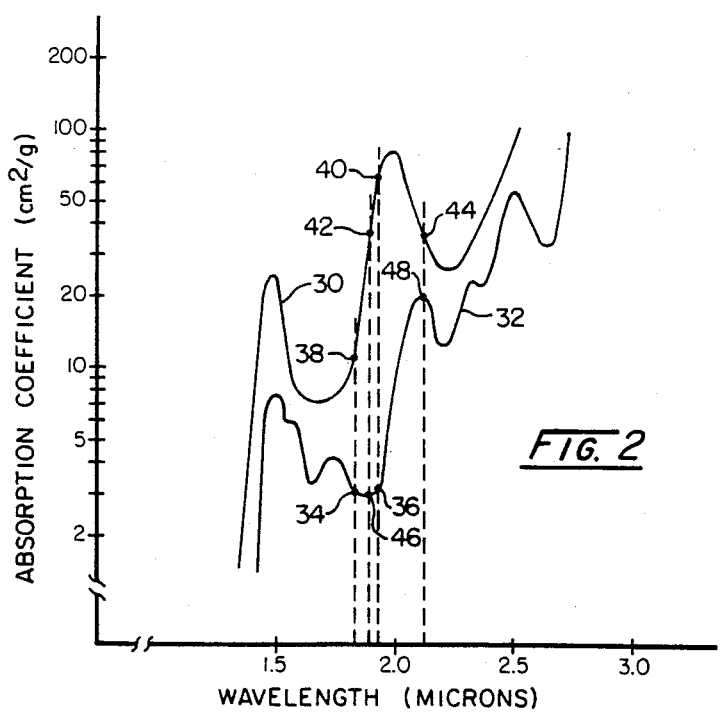
FIG. 2 is a semi-logarithmic plot of infrared radiation absorption coefficients for water and cellulose, as a function of wavelength, illustrating the manner of wavelength selection for the purpose of carrying out the invention.

In FIG. 2, the curve 30 shows the absorption coefficient of water (in square centimeters per gram) as a function of infrared wavelength in microns, and similarly the curve 32 shows the coefficient for cellulose.

As shown by the intersection points 34 and 36, the first set of wavelengths 22 and 24 (1.83μ and 1.93μ) have about the same absorption coefficients for the cellulose (fiber) constituent. However, as shown by the intersection points 38 and 40 these wavelengths have substantially different absorption coefficients for the moisture contained in the paper.

As shown by the intersection points 42 and 44, the second set of wavelengths 26 and 28 (1.89μ and 2.12μ) have about the same absorption coefficients for the moisture contained in the paper. However, as shown by the intersection points 46 and 48, these wavelengths have substantially different coefficients for the cellulose fiber constituent.

In FIG. 1 the radiations 22, 24, 26 and 28 are shown to be detected by the detector 16. The detector 16 is part of a data acquisition system 50 that may be similar to apparatus described in U.S. Pat. No. 4,300,049 Sturm. System 50 produces responses 52, 54, 56 and 58 indicative of the transmittances of the detected radiations at the respective wavelengths 22, 24, 26 and 28. Each transmittance value represents the ratio of the radiation intensity transmitted to the detector 16 with the paper 10 in position, to the radiation intensity transmitted to the detector without the paper 10 in the radiation path. The transmittance values indicated by responses 52, 54, 56 and 58 may be conventionally provided either in the form of electrical signals or in the form of numbers to be stored in the memory of a digital computer.

At 60, a function of the ratio of the transmittances of the detected radiations in the first set 18 is formed to produce a first response 62 to the moisture contained in the paper 10. This first rsponse 62 is typically represented mathematically by:

$$\frac{R_{1.83}}{A_{1.93}} - 1 = aW^*f(F) \quad (1)$$

Here $R_{1.83}$ is the transmittance at the reference wavelength 1.83μ; $A_{1.93}$ is the transmittance at the water absorption wavelength 1.93μ; a is a constant determined in calibration; W is the weight per unit area of moisture contained in the paper sheet 10, and f(F) is a first error function that is dependent on the scattering characteristic and broadband absorber (e.g., carbon) content of the fiber constituent in the paper.

At 64, a function of the ratio of the transmittances of the detected radiations in the second set is formed to produce a second response 66 to the fiber constituent contained in the paper. This second response is typically represented mathematically by:

$$\frac{R_{1.89}}{A_{2.12}} - 1 = b(F + \delta W)^*f(F) \quad (2)$$

Here $R_{1.89}$ is the transmittance at the reference wavelength 1.89μ; $A_{2.12}$ is the transmittance at the cellulose fiber absorption wavelength 2.12μ; b is a constant determined in calibration; F is the fiber weight per unit area; f(F) is substantially the same first error function previously defined, and δW is a second error function dependent on the amount of moisture contained in the paper.

The error function δW is almost inevitable because even though apparently the best possible choice of wavelengths has been made to provide water independence in the fiber (cellulose) measurement, as shown by point 42 (FIG. 2) in particular (as well as point 44) the instrument is working on the slope of the water absorption band.

Referring again to FIG. 1, there is formed at 68 a function of the ratio of the first and second responses 62 and 66 to produce a third response $G_r$ that is substantially independent of the first error function f(W) but is dependent on the second error function δW. That is, $$G_r = \frac{aW}{b(F + \delta W)} \quad (3)$$

The basis weight, or total weight per unit area of the paper is substantially equal to the sum F+W of the fiber and water weights, and hence:

$$G_r = \left(\frac{a}{b}\right) \frac{\frac{W}{F+W}}{\frac{F}{F+W} + \delta \frac{W}{F+W}} = \left(\frac{a}{b}\right) \frac{\%M}{\%F + \delta\%M} \quad (4)$$

where %F is the percent fiber in the paper and %M is the percent moisture.

Since %F = 1 − %M, $$G_r = \left(\frac{a}{b}\right) \frac{\%M}{(1 - \%M + \delta\%M)} = \left(\frac{a}{b}\right) \frac{\%M}{1 + \%M(\delta - 1)} \quad (5)$$

Letting δ − 1 = δ′

$$\%M = \frac{G_r\left(\frac{b}{a}\right)}{1 - \delta' G_r\left(\frac{b}{a}\right)} \quad (6)$$

As illustrated in FIG. 1., the calculation of equation (6) is implemented at 70. Here the third response $G_r$ is utilized together with calibration constants a, b and $\delta'$ to produce a fourth response 72 which is a function of the third response $G_r$, and which is calibrated in accordance with the second error function $\delta W$. The response 72 is indicative of the moisture fraction or percent moisture %M contained in the paper, substantially independent of the first and second error functions, and substantially independent of variations of the scattering characteristic and variations in the amount of the broadband absorber.

In calibrating the instrument, an iterative digital computer program may be used to determine the values for the constants a, b and $\delta'$ which make equation (6) best fit the laboratory-determined moisture values for a number of actual paper samples.

While the invention has been described and illustrated by particular procedures and particular apparatus, the showing and description is meant to be illustrative only and not restrictive, since many changes and modifications can be made without departing from the spirit and scope of the invention.

What is claimed is:

1. A method adapted for measuring the moisture fraction or percent moisture contained in a traveling sheet of paper also containing a fiber constituent that may have a variable infrared radiation scattering characteristic and may include a variable amount of a broadband infrared radiation absorber, which method comprises directing into the paper two sets of infrared radiation wavelengths that are affected to about the same extent by the variable scattering characteristic and are also affected to about the same extent by the variable amount of the broadband absorber,
   the first set including wavelengths that have about the same absorption coefficients for the fiber constituent but have substantially different absorption coefficients for the moisture contained in the paper,
   the second set including wavelengths that have about the same absorption coefficients for the moisture contained in the paper but have substantially different absorption coefficients for the fiber constituent,
   detecting radiations from the paper,
   forming a function of the ratio of the transmittances of the detected radiations in the first set to produce a first response to the moisture contained in the paper, the first response including a first error function dependent on the scattering characteristic and broadband absorber content of the fiber constituent,
   forming a function of the ratio of the transmittances of the detected radiations in the second set to produce a second response to the fiber constituent, the second response including substantially the same first error function dependent on the scattering characteristic and broadband absorber content of the fiber constituent, the second response also including a second error function dependent on the amount of moisture contained in the paper,
   forming a function of the ratio of the first and second responses to produce a third response that is substantially independent of the first error function but is dependent on the second error function, and
   producing a fourth response which is a function of the third response, which is calibrated in accordance with the second error function, and which is indicative of the moisture fraction or percent moisture contained in the paper, substantially independent of the first and second error functions and substantially independent of variations of the scattering characteristic and variations in the amount of the broadband absorber.

2. A method as in claim 1 wherein the first set of infrared wavelengths are about 1.83$\mu$ and 1.93$\mu$ and wherein the second set of infrared wavelengths are about 1.89$\mu$ and 2.12$\mu$.

3. Apparatus adapted for measuring the moisture fraction or percent moisture contained in a traveling sheet of paper also containing a fiber constituent that may have a variable infrared radiation scattering characteristic and may include a variable amount of a broadband radiation absorber, which apparatus comprises means for directing into the paper two sets of infrared radiation wavelengths that are affected to about the same extent by the variable scattering characteristic and are also affected to about the same extent by the variable amount of the broadband absorber,
   the first set including wavelengths that have about the same absorption coefficients for the fiber constituent but have substantially different absorption coefficients for the moisture contained in the paper,
   the second set including wavelengths that have about the same absorption coefficients for the moisture contained in the paper but have substantially different absorption coefficients for the fiber constituent,
   means for detecting radiations from the paper,
   means for forming a function of the ratio of the transmittances of the detected radiations in the first set to produce a first response to the moisture contained in the paper, the first response including a first error function dependent on the scattering characteristic and broadband absorber content of the fiber constituent,
   means for forming a function of the ratio of the transmittances of the detected radiations in the second set to produce a second response to the fiber constituent, the second response including substantially the same first error function dependent on the scattering characteristic and broadband absorber content of the fiber constituent, the second response also including a second error function dependent on the amount of moisture contained in the paper,
   means for forming a function of the ratio of the first and second responses to produce a third response that is substantially independent of the first error function but is dependent on the second error function, and
   means for producing a fourth response which is a function of the third response, which is calibrated in accordance with the second error function, and which is indicative of the moisture fraction or percent moisture contained in the paper, substantially independent of the first and second error functions and substantially independent of variations of the scattering characteristic and variations in the amount of the broadband absorber.

4. Apparatus as in claim 3 wherein the first set of infrared wavelengths are about 1.83$\mu$ and 1.93$\mu$ and wherein the second set of infrared wavelengths are about 1.89$\mu$ and 2.12$\mu$.

* * * * *